United States Patent
Mitra et al.

(10) Patent No.: US 12,262,896 B2
(45) Date of Patent: Apr. 1, 2025

(54) SYSTEM AND METHOD FOR TRACKING RESECTION PLANES

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Riddhit Mitra, Pittsburgh, PA (US); Branislav Jaramaz, Pittsburgh, PA (US); Samuel Dumpe, Beaver, PA (US); Constantinos Nikou, Monroeville, PA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 94 days.

(21) Appl. No.: 17/056,660

(22) PCT Filed: May 20, 2019

(86) PCT No.: PCT/US2019/033077
§ 371 (c)(1),
(2) Date: Nov. 18, 2020

(87) PCT Pub. No.: WO2019/222728
PCT Pub. Date: Nov. 21, 2019

(65) Prior Publication Data
US 2021/0204963 A1   Jul. 8, 2021

Related U.S. Application Data

(60) Provisional application No. 62/673,575, filed on May 18, 2018.

(51) Int. Cl.
*A61B 17/15*   (2006.01)
*A61B 34/20*   (2016.01)

(52) U.S. Cl.
CPC .......... *A61B 17/157* (2013.01); *A61B 17/155* (2013.01); *A61B 34/20* (2016.02); *A61B 2034/2055* (2016.02)

(58) Field of Classification Search
CPC .......... A61B 17/157; A61B 2034/2055; A61B 34/20
See application file for complete search history.

(56) References Cited

U.S. PATENT DOCUMENTS 6,514,259 B2   2/2003   Picard et al.
6,757,582 B2   6/2004   Brisson et al.
7,670,345 B2   3/2010   Plassky et al.
(Continued)

FOREIGN PATENT DOCUMENTS

EP   1430842 A1   6/2004
EP   2143391 A1   1/2010
(Continued)

OTHER PUBLICATIONS

European Patent Office, First Examination Report, dated Mar. 21, 2024, 5 pages.

*Primary Examiner* — Samuel S Hanna
(74) *Attorney, Agent, or Firm* — ArentFox Schiff LLP; Joseph M. Maraia

(57) ABSTRACT

A system for tracking resection planes during a surgical procedure includes a cutting block and a position tracker. The cutting block is configured to be mounted on an anterior surface of a bone during the surgical procedure. The cutting block comprises at least one slot configured to position a resection tool during the surgical procedure. The position tracker is configured to be directly attached to the cutting block after the cutting block is mounted on the anterior
(Continued)

surface to allow positional tracking of the cutting block by a tracking device during the surgical procedure.

14 Claims, 7 Drawing Sheets

(56) References Cited

U.S. PATENT DOCUMENTS

| | | |
|---|---|---|
| 7,776,048 B2 | 8/2010 | Neubauer et al. |
| 8,961,536 B2 | 2/2015 | Nikou et al. |
| 9,168,106 B2 | 10/2015 | Boyer et al. |
| 2003/0028196 A1* | 2/2003 | Bonutti .............. A61G 13/0054 606/87 |
| 2005/0154394 A1* | 7/2005 | Michalowicz ....... A61B 17/157 606/87 |
| 2005/0190380 A1* | 9/2005 | Plassky ................. A61B 90/36 356/614 |
| 2005/0203528 A1* | 9/2005 | Couture ................ A61B 90/11 606/86 R |
| 2005/0261699 A1* | 11/2005 | Neubauer .............. A61B 90/11 606/96 |
| 2006/0217733 A1* | 9/2006 | Plassky .................. A61B 90/92 606/87 |
| 2008/0010706 A1* | 1/2008 | Moses .................... A61B 34/30 600/407 |
| 2010/0016859 A1* | 1/2010 | Plassky ................ A61B 17/157 606/87 |
| 2010/0064216 A1* | 3/2010 | Borja ................. A61B 17/1764 715/705 |
| 2010/0305711 A1* | 12/2010 | McKinnon ........... A61B 17/157 606/82 |
| 2012/0330135 A1* | 12/2012 | Millahn ................ A61B 34/20 600/424 |

FOREIGN PATENT DOCUMENTS

| | | |
|---|---|---|
| FR | 2838627 A1 | 10/2003 |
| WO | 2011107147 A1 | 9/2011 |
| WO | 2018162518 A1 | 9/2018 |

* cited by examiner

SYSTEM AND METHOD FOR TRACKING RESECTION PLANES

CROSS-REFERENCE TO RELATED APPLICATIONS

This application is a U.S. national stage filing under 35 U.S.C. § 371 of International PCT Application No. PCT/US2019/033077, filed May 20, 2019, which claims the benefit of priority to U.S. Provisional Patent Application No. 62/673,575 titled "SYSTEM AND METHOD FOR TRACKING RESECTION PLANES," filed May 18, 2018, each of which is incorporated herein by reference in its entirety.

TECHNICAL FIELD

The present disclosure is generally related to apparatuses, systems and methods for computer-aided orthopedic surgery. More specifically, the present disclosure is related to automatically determining the position and orientation of an implant for a patient in advance of joint replacement surgery.

BACKGROUND

The use of computers, robotics, and imaging to aid orthopedic surgery is known in the art. There has been a great deal of study and development of computer-aided navigation and robotic systems used to guide surgical procedures. For example, a robotic surgery system can assist the surgeon in accurately cutting a bone into a desired shape. In procedures such as total hip replacement (THR), computer-aided surgery techniques have been used to improve the accuracy and reliability of the surgery. Orthopedic surgery guided by images has also been found useful in preplanning and guiding the correct anatomical position of displaced bone fragments in fractures, along a good fixation by osteosynthesis.

Cut guides or cutting blocks can be used in an orthopedic surgical procedure to assist a surgeon in cutting or modifying some portions of a target bone. For example, in joint replacement surgeries, such as THR or total knee replacement (TKR), the preparation of the bones can involve temporarily affixing saw guide cutting blocks to the bones so that a reciprocating saw blade can be held steady along its intended path. Placement of these blocks can be guided by manual instrumentation or through the use of jigs.

The positioning of cutting blocks can be a time consuming and complicated process, which is critical to positive outcomes for the patient. Mechanisms that allow the cutting blocks to be adjusted within the required workspace are complex, and require high machining tolerances, adding to the costs and complexity of these instrument systems. Such instruments are also expensive to create and manage, and result in significant operational costs to maintain and clean. These costs increase the burden of managing cutting blocks. Mechanical referencing instruments can also add to the burden of managing cut guides and cutting blocks.

Manual alignment of these cutting blocks can be cumbersome and is limited to information obtainable through mechanical and visual referencing means. The instruments used to manually align cutting blocks cannot fully capture the 3D shape of the bones, nor can they adequately capture information about kinematics of the joint or soft tissue tension or laxity.

Some surgery tracking systems and robotic-assisted surgery techniques include tracking rigid bodies with fixation pins for attachment and tracking of the femur and tibia bones in orthopaedics. Typically, 3-5 mm bi-cortical bone screws or smaller uni-cortical screws are inserted into the patient's bone(s) for tracker attachment. The tracker can then be registered and, by measuring movement of the tracker in space, the surgery tracking system can accurately measure the location of the patient during a procedure. However, the attachment of the tracker can be an added burden during the surgical procedure. Use of these screws can also be considered an undesirable addition to the invasiveness of the surgery.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
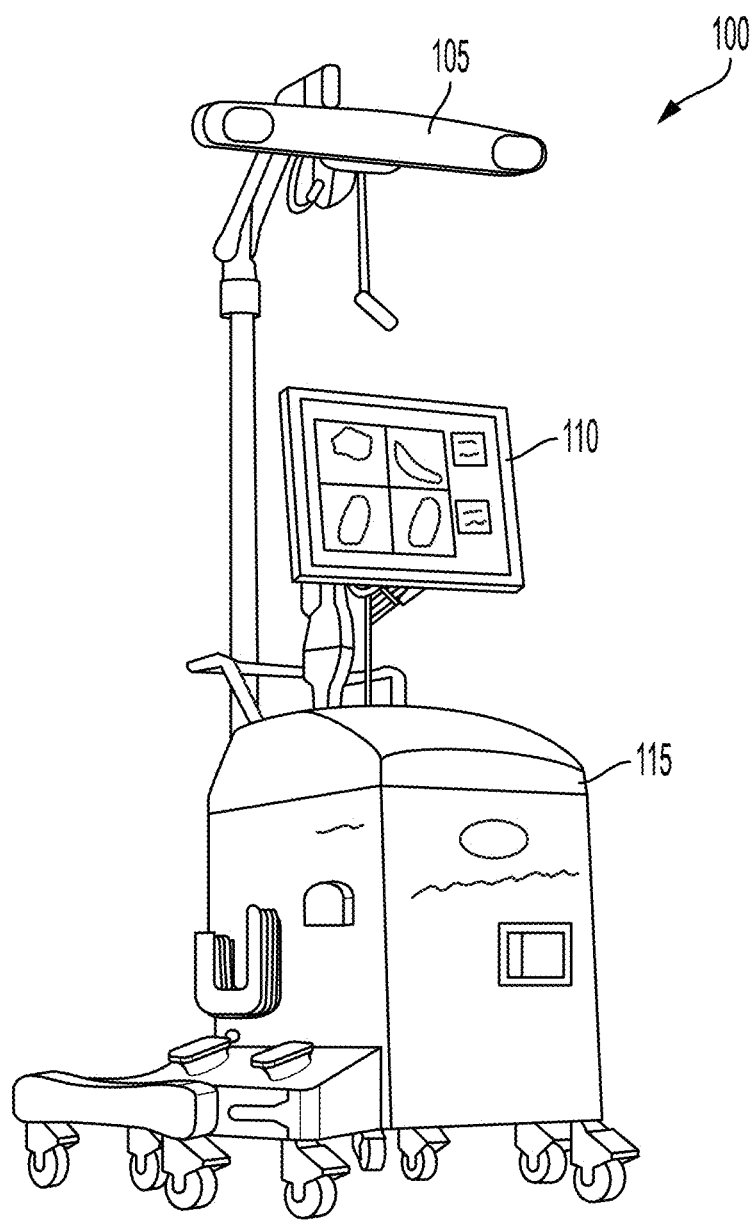
FIG. 1 depicts an illustrative navigation system in accordance with certain embodiments.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Total knee replacement surgery requires several precise cuts to be made in the femur and tibia in order for the chosen implant to fit correctly and to restore the geometry and kinematics of a natural healthy knee. To perform these steps, in both conventional (manual method) and Computer Aided Surgery (CAS) total knee replacement, a series of guide blocks are used that provide a drill or cutting guide to assist the surgeon to perform the steps required to prepare the femur and tibia for receiving the implant.

The conventional manual instrumented method used to prepare the femur for a knee replacement implant, outlined below as an example, generally includes fastening a distal cutting guide block on the femur, generally located by an intramedullary pin (IM rod) or screw inserted into the distal end of the femur and locating the distal guide block in the desired position, such position providing the correct implant varus-valgus and transverse rotational angle about the IM rod and the proper amount of distal resection; aligning a distal cutting guide, whether being integral with the guide block or a separate element configured to fasten thereto, in a predetermined location relative to the distal guide block reference position and inserting locating pins through the distal cutting guide and into the femoral condyles to fasten the cutting guide in place on the anterior surface; making the distal cut to resect the predetermined amount of bone from the distal end of the condyles; positioning a second femoral implant sizing guide (the femoral sizer) freely on the newly cut distal surface of the femur and ensuring that the anticipated resection level for the anterior cut, the anterior-posterior adjustment (referencing off either the existing posterior condyle or the anterior femur) for correct implant sizing, and that the rotational alignment and medial-lateral position of the positioning block are all correct before fixing the 4-in-1 cutting guide block in place with pins, drilling the implant peg holes; and performing the anterior and posterior cuts, and subsequently making the anterior-posterior chamfer and notch cuts. Note that adjusting rotation of the implant in the sagittal plane is generally not possible with the IM rod based instruments typically in use today. Thus, a femoral implant's position in knee extension is normally set in a fixed relationship to the IM rod axis.

The steps required to prepare the tibia are less involved. Generally, they include: aligning a guide rail relative to the mechanical axis of the tibia; obtaining proper rotational (varus-valgus) alignment of a guide block attached to the guide rail, and fastening it in place to the anterior surface of the proximal end of the tibia; further adjusting the vertical and angular position of the tibial guide block to ensure that the desired posterior slope and level of tibial resection are provided; inserting location pins using the guide block to fix its position on the tibia; removing the guide block and replacing it with a tibial resection cutting guide that is retained in place with the location pins; and resecting the chosen amount of tibial bone. Note that the final position of the tibial plate implant is not determined by this step, only the planar surface on which it will rest. Anterior-posterior (AP), medial-lateral (ML), and rotational positioning of the tibial plate implant are subsequently determined by the surgeon's judgment as to its best fitting location on the resected tibia after the femoral implant has been located and fixed to the resected femur.

The above described surgical procedure remains generally similar whether traditional or computer assisted surgery is being performed. A CAS system can employ passive or active trackable elements affixed to surgical tools and patient bone references to permit the determination of position and orientation of these tools and bones in three-dimensional space. In certain types of CAS, preoperatively taken images or computer generated models created from preoperative patient scans can be used to provide accurate patient specific anatomical information. The images or models can be used to register or calibrate the real-time position of the same patient's anatomical elements. This can permit subsequent tracking of the patient's anatomical elements and display of these anatomical elements relative to the surgical tools used during the surgery.

As noted above, when mounting tracking attachments for computer aided surgery, the position trackers are typically pinned directly to the bone. Thus, for a knee replacement surgery, a femur tracking attachment is pinned to the patient's femur, and a tibia tracking attachment is pinned to the patient's tibia. The attachment of the pins for the tracking attachments not only add to the setup time for the procedure, but also increase the risk of infection and fracture. Fracture risk becomes an increasingly likely outcome when dealing with a smaller bone such as the tibia.

The present disclosure is directed to techniques for mounting a tracker or tracking attachment directly to a previously mounted cut guide during a joint replacement procedure. For example, in a total knee replacement, the tibia tracker can be directly mounted to a previously mounted tibia cut guide, thereby eliminating a need to pin the tibia tracker to the patient's tibia itself. As described in greater detail below, standard ankle clamps and extramedullary alignment guides can be used to position the tibia cut guide according to standard mounting procedures. Once the tibia cut guide is attached, the tibia tracker can be attached directly to the tibia cut guide and used to provide anatomic and soft tissue data to the navigation or robotic-assisted surgical system, such as the navigation system described below in the description of FIG. 1.

FIG. 1 depicts an illustrative navigation system in accordance with certain embodiments. As shown in FIG. 1, the navigation system 100 can include a tracking device 105. In some embodiments, the navigation system 100 can further include a display 110 and a processing system 115.

In certain implementations, the tracking device 105 can include an infrared camera that identifies the location of position trackers, such as femur and tibia trackers as described herein, to determine the position and orientation of the patient's extremity during, for example, a surgical procedure. For example, the position trackers and the tracking device 105 can be used to identify and provide data relevant to the precise location of the bones in the knee joint. In certain embodiments, the tracking device 105 can detect tracking spheres or other similar markings located on the position trackers in order to gather location data regarding a patient's femur, tibia, or other bone.

In an embodiment, a navigation system 100 can also be used in conjunction with a surgical device having a plurality of position trackers (not shown) to enable the accurate placement and orientation of a cutting block and/or an implant device in accordance with the teachings herein. For example, the navigation system 100 can be used during the surgical procedure to guide and direct the surgeon in order to place an implant within a patient's joint.

In an embodiment, the display 110 of the navigation system 100 can be used to provide feedback information regarding various aspects of the surgical procedure, such as the orientation of the surgical device, the proper location of the implant device, or the like. Further, the processing device 115 of the navigation system 100 can be used to determine the position and orientation of the surgical device with respect to a patient in substantially real time. Additional features and description of the navigation system 100 can be found in, for example, U.S. Pat. Nos. 6,757,582 and 8,961, 536, both of which are incorporated herein by reference in their entireties.

Figure 2:
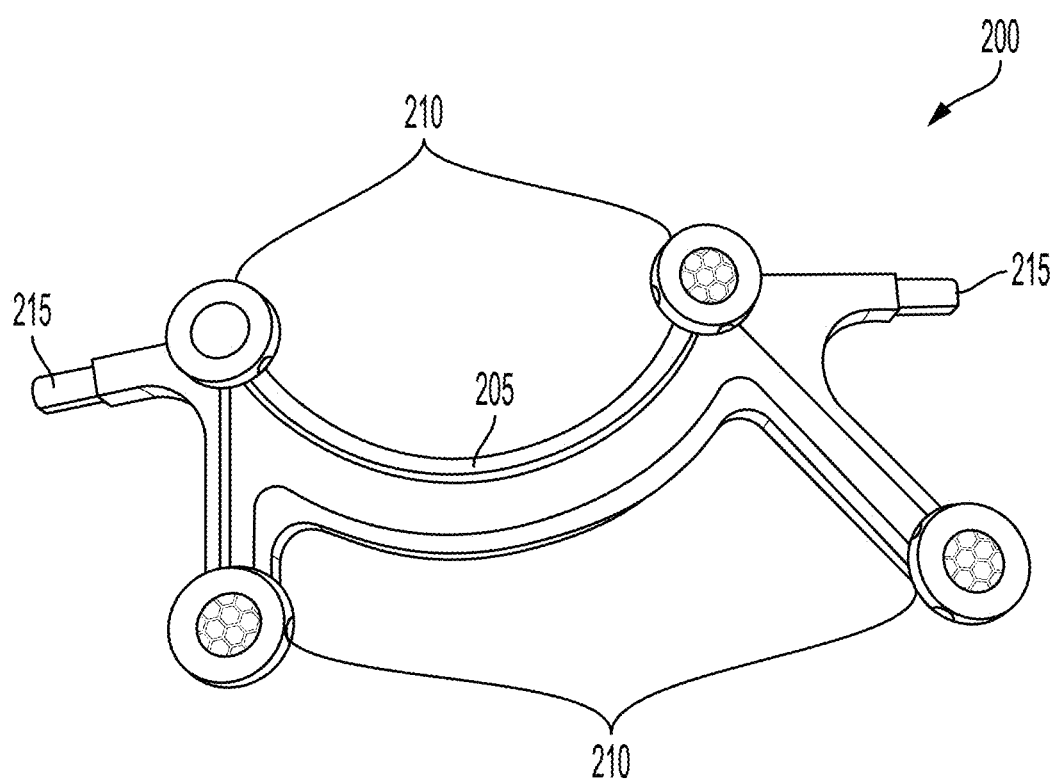
FIG. 2 depicts an illustrative tracking attachment for use with a navigation system, such as that described in FIG. 1, in accordance with certain embodiments.

FIG. 2 illustrates a sample position tracker 200 similar to those described above in, for example, the discussion of FIG. 1. However, as noted herein, the position tracker 200 can be modified from a standard position tracker. For example, the position tracker 200 can be designed to be mounted to another rigidly fixed component, such as a cut guide. As such, rather than being configured to be pinned directly to a patient's bone (e.g., a patient's tibia), position tracker 200 can be configured to be mounted directly to a tibia cut guide.

As shown in FIG. 2, the position tracker 200 can include a frame 205. The frame 205 can be shaped to accommodate multiple position markers 210. For example, as shown in FIG. 2, a set of four position markers 210 are mounted on the frame 205, positioned at various points about a general periphery of the frame. The position markers 210 can include a reflective portion or another similarly recognizable portion configured to be identified and tracked by a tracking device, such as tracking device 105 as described above in the discussion of FIG. 1.

It should be noted that four position markers 210 are shown in FIG. 2 by way of example only. Depending upon the size and shape of the position tracker 200, alternate numbers of position markers 210 can be used. However, it should be noted that to maintain an accurate measurement of where the position tracker is located and how it is oriented, the position tracker should ideally include multiple position markers such that a navigation system tracking the position tracker has more data points to monitor and track through space.

The frame 205 can further include one or more mounting points 215. As noted above, the position tracker 200 can be configured to mount directly to a cut guide such as a tibia cut guide. In such an implementation, the mounting points 215 can be configured to rigidly fix the position tracker 200 to the cut guide. Depending upon the design of the position tracker 200, the mounting points 215 can be statically designed and configured to be frictionally held in place by, for example, a clamp integrated into or removably attached to the cut guide. In alternate implementations, the position tracker 200 can be configured such that the mounting points 215 include clamps or other similar fixation devices for directly attaching the position tracker to the cut guide.

Figure 3:
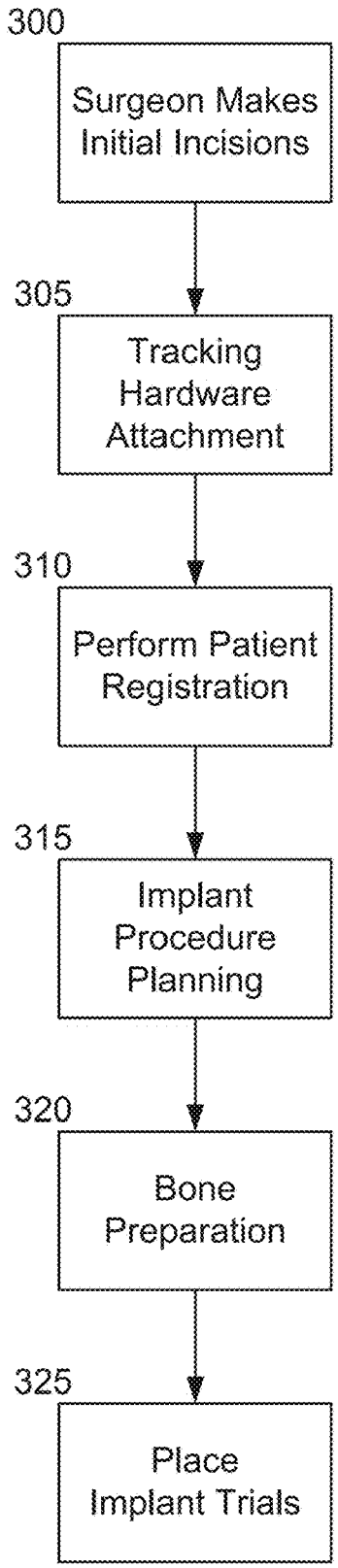
FIG. 3 depicts a flow diagram of an illustrative method of performing a joint replacement surgery in accordance with certain embodiments.

FIG. 3 illustrates a flowchart showing a sample surgical procedure for a total knee replacement. It should be noted that, while the discussion and examples included herein are generally directed to knee replacement procedures, the techniques described herein related to position tracker mounting on a previously mounted component, such as a cut guide, can be incorporated into other computer assisted surgical procedures where a navigation system such as that described above in regard to FIG. 1 is used.

Referring to FIG. 3, the process as illustrated therein begins after all pre-surgery preparation and planning has already been performed. Following standard approaches and accepted surgical techniques, the surgeon can make 300 the initial surgical incisions on the indicated patient for knee replacement. After the initial incisions, the surgeon can proceed to attach 305 the tracking hardware (e.g., a femur position tracker and a tibia position tracker). Using existing manual tools, which can include the ankle clamp, extramedullary alignment guide and tibia cut guides with resection depth gauge, the surgeon can follow surgical technique guidance to mechanically align the cut guide on the patient's tibia bone. The surgeon utilizes pins to secure the standard tibia cutting guide on the bone surface at this time. The surgeon can further attach femur fixation pins for tracking the femur using the navigation system and use the tibia cutting guide as a fixation base to attach the tibia position tracker.

Figure 4:
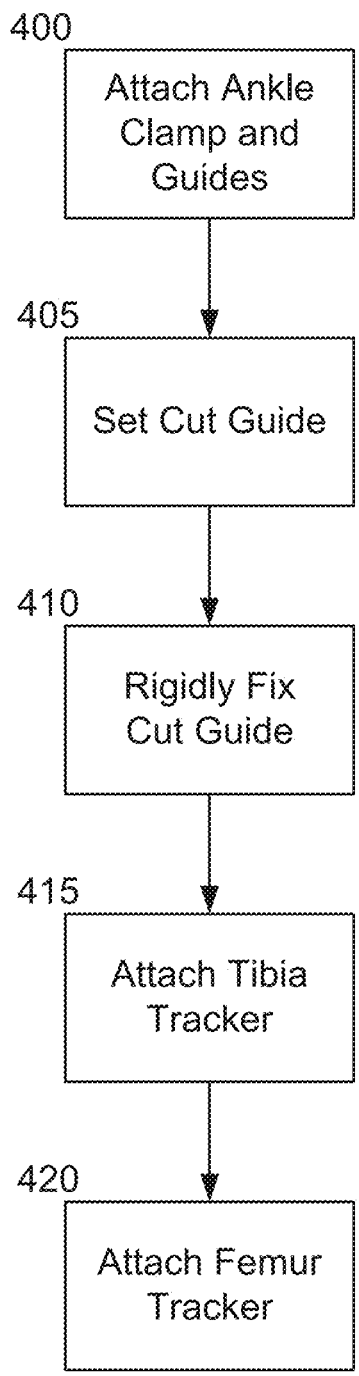
FIG. 4 depicts a flow diagram of an illustrative method of attaching tracking hardware in accordance with certain embodiments.
Figure 5:
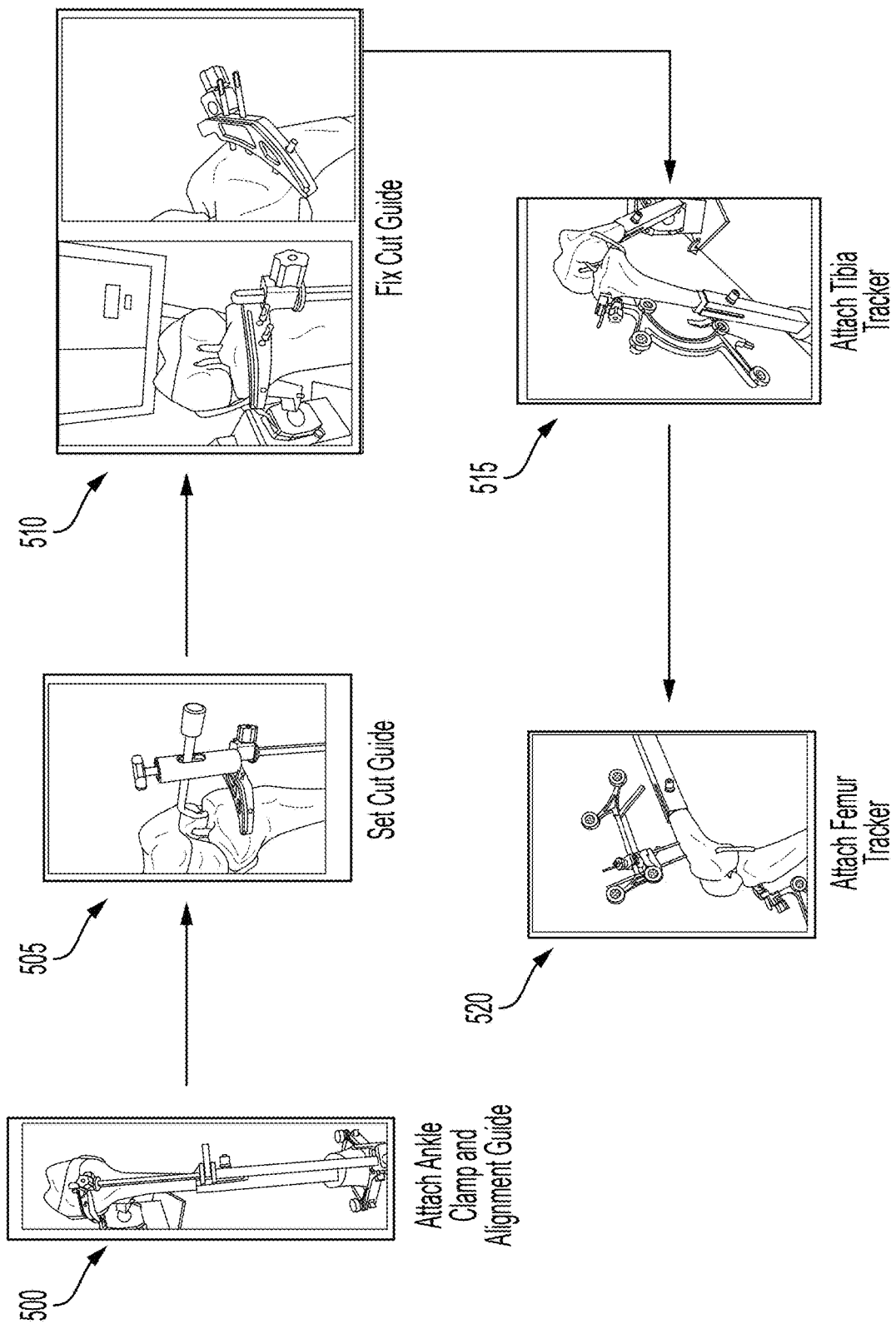
FIG. 5 depicts a similar flow diagram as shown in FIG. 4 further illustrated with annotated photos of attaching the tracking hardware in accordance with an embodiment.

FIGS. 4 and 5 provide additional detail for the position tracker attachment. FIG. 4 illustrates a process for position tracker attachment using a series of process steps, while FIG. 5 illustrates the same process using photos showing the tracker attachment on a skeleton's tibia and femur. The process as shown in FIGS. 4 and 5 can be implemented, for example, during the tracker attachment operation 305 of FIG. 3 as described above.

Referring initially to FIG. 4, the surgeon can attach 400 an ankle clamp and extramedullary alignment guide to the patient's lower leg. The surgeon can rotate and properly position the ankle clamp and guide such that a desired angle and position is achieved. Once the proper angle and position is achieved, the surgeon can set 405 the tibia cut guide. Setting 405 the tibia cut guide can include, for example, setting the desired resection depth, varus/valgus angles, and slope for the tibia. Once the cut guide is set 405, the cut guide can be rigidly affixed 410 to the patient's tibia using pins as described above. The ankle clamp and extramedullary alignment guide can then be removed.

Once the cut guide is rigidly affixed 410, the surgeon can attach 415 the tibia position tracker directly to the mounted cut guide. As noted above in the discussion of FIG. 2, the tibia position tracker can be clamped or otherwise removably attached to the cut guide. The surgeon can then attach 420 the femur position tracker using conventional attachment techniques including, for example, directly pinning the femur position tracker to the patient's femur.

Referring to FIG. 5, in photo 500 the ankle clamp and extramedullary alignment guide can be affixed to the patient's lower leg. The surgeon can use their best judgment and experience to properly position the guide at a desired angle and location. As shown in photo 505, the surgeon can then set the cut guide to the proper position. As noted above, this can include setting the desired resection depth, varus/valgus angles, and slope. As shown in the left photo of 510, the pins are inserted into the cut guide to rigidly fix the cut guide to the patient's tibia. In the right photo of 510, the extramedullary alignment guide and ankle clamp have been removed, leaving only the cut guide fixed to the tibia. In photo 515, the tibia position tracker (e.g., tracker 200 as described above) can be attached to the cut guide. As shown in photo 515, the tibia position tracker is clamped into the same hole into which the extramedullary alignment guide was previously attached. In alternate implementations, the cut guide can include a separate attachment point for the tibia position tracker.

As shown in photo 520 of FIG. 5, the femur position tracker can be attached to the patient's femur using traditional attachment techniques including, for example, directly pinning the femur position tracker to the patient's femur.

Referring again to FIG. 3, the process can continue with the surgeon beginning the intraoperative procedure with the computer assisted surgical system. The surgeon can perform registration 310 of the patient using the mounted tracking hardware and the navigation system components of the computer assisted surgical system. During registration, attention to detail is critical to achieve high-accuracy registration of the bone model. The surgeon can also register 310 the soft tissue constraints of the knee using, for example, a joint laxity input stage in the intraoperative workflow.

The surgeon, along with the surgical system, can then plan 315 the size and position of the implant components while factoring in the impact on soft-tissue space. This calculation can be at least partially based on the joint laxity definition provided during registration. Because the tibia tracker is rigidly attached to the cut guide for the tibia, the "default" cut plane location based on the guide position can be included in the planning information. In certain implementations, this plane can be determined by placing the tracked plane in the cutting slot of the tibia guide, or it can be derived from a known unique geometric relation between the tibia position tracker and the cutting guide. By knowing the location of the tibia resection plane during this planning stage, the surgeon and/or surgical system can proceed with adjusting the remaining parameters to optimize the knee alignment and balance. Alternately, the surgeon and/or surgical system can manipulate the parameters for the plane to fine tune the implant position for additional slope or depth of resection as needed to virtually balance the joint for desired cut results.

The surgeon can then begin bone preparation 320. The preparation 320 can include bone removal/resection utilizing, for example, computer-assisted techniques for preparing the femur. The surgeon can, for example, insert locking posts on the femur bone using a handheld robotic controlled bur. One or more femur cut guides can then be mounted on the locking posts, and the surgeon can utilize the computer assisted surgical system guides to make saw cuts that replicate the planned position of the femur implant. The surgeon can also cut the tibia using the previously-mounted tibia cut guide. In certain implementations, the surgeon can confirm with the computer assisted surgical system that the tibia cut guide is properly positioned (e.g., at the proper plane and angle). If the position is confirmed, the surgeon can then make the tibial cut. If, for some reason, additional cutting is required, the surgeon can use the handheld robotic controlled bur to fine tune the tibia cut of the tibial implant placement.

Following bone preparation and removal, the surgeon can place 325 the implant trials on the prepared bone, and re-tension the ligaments of the joint to assess achieved joint laxity. At this point, the surgeon can also go back to planning whether to re-adjust the cuts, based on achieved alignment and balance. The surgeon can then execute any additional cuts using, for example, robotic-assisted burring.

It should be noted that the process shown in FIG. 3 and the related process shown in FIGS. 4 and 5 are provided by way of example only. In certain implementations, various process steps can be modified or performed in an alternate order. For example, the surgeon may opt to cut the tibia once the tibia cut guide is fixed to the bone, and prior to attachment of the tibia position tracker. In such an example, the surgeon can also opt to place the implant on the tibia prior to registration. The registration process can then be performed as described above with respect to the femur and remaining soft tissue.

Similarly, during planning, the surgeon can change the position of the femur to balance joint laxity as well as fit anatomy for optimized outcomes (that can already include the tibia implant in the joint laxity). Additionally, in certain implementations, if beneficial for optimal joint balancing and alignment, the surgeon can further adjust the tibia depth, slope, and varus/valgus of cut during the planning stage for robotic-assisted preparation of the final surface during the bone preparation.

In certain additional implementations, performing a surgical procedure such as TKA can include making an initial tibia resection to relieve any restrictions in the joint. The position of the initial resection can be determined by tracking the position of the cutting device making the cut or by registering the cut location using a tracked measuring device such as a plate probe or other similar measuring device. This initial resection information can be used as a starting point for joint simulations that include updated joint laxity tests. Various parameters for the joint replacement such as proper tray placement in the plan of the initial resection, bearing options, possible implant component sizes and positions, and other similar parameters can be refined for a specific surgical plan based upon the updated test information.

Figure 6:
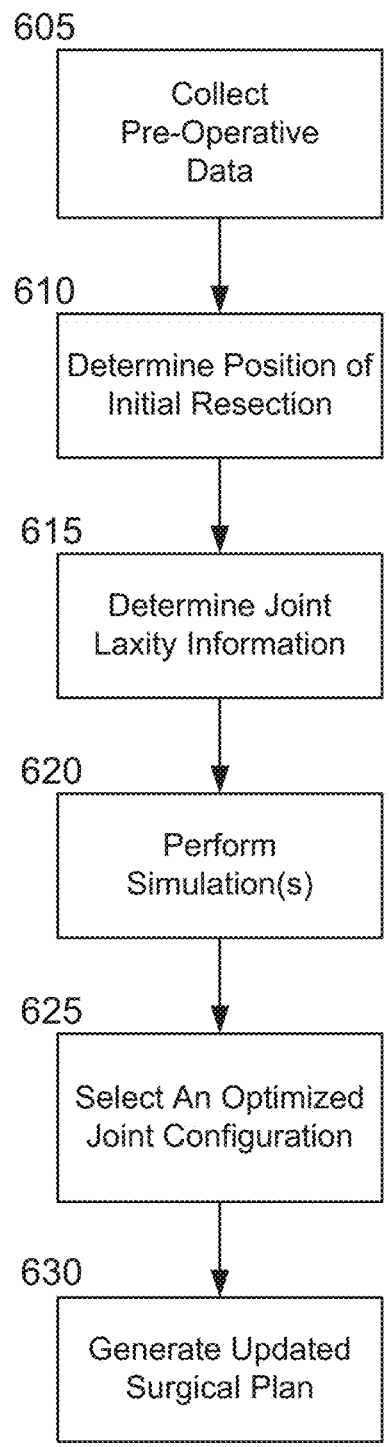
FIG. 6 depicts a flow diagram of an illustrative method of performing an initial tibia resection in accordance with certain embodiments.

For example, a sample process for performing knee replacement surgery incorporating an initial tibia resection as taught herein is shown in FIG. 6. In certain implementations, a CAS system can collect 605 pre-operative data. For example, reflective bone trackers, such as position tracker 200 described above, can be attached to the tibia and the femur. In certain implementations, the tibia tracker can be attached using the process described above in reference to FIGS. 4 and 5. Once the trackers are attached, the tibia can be moved such that the knee is moved through a full range of motion. A navigation system operably connected to the CAS system can collect information related to the movement of the trackers during the range of movement and transmit the information to the CAS system.

Additionally, once the trackers are attached, a surgeon can make an initial resection in the tibia to relieve any restrictions in the joint. For example, the initial resection can remove any access or abnormal bone on the tibia that is impinging movement against the femur. Additionally or alternatively, the initial resection can also be positioned such that it corresponds to an initial tibia cut in a surgical plan for a knee replacement procedure.

By using navigated surgical instruments, the CAS system can determine 610 the position of the initial resection. For example, the position of the initial tibia resection can be determined by tracking the cutting device making the resection. In some examples, the initial resection can be made using a cut guide having a known location (e.g., using techniques described above). In certain implementations, a measuring device such as a plate probe can be used to measure the position of the initial resection. This measurement can include an accurate measurement of both the depth of the initial resection (e.g., providing an indication of how much bone was removed during the initial resection) as well as the angle of the initial resection. Based upon this known location, the CAS system can accurately determine 610 the position of the initial resection.

Following the initial resection, the tibia can again be moved such that the knee is moved through its full range of motion. However, in this instance, since the initial resection has relieved any restrictions in the joint, the CAS system can determine 615 joint laxity information by tracking the movement of the tibia with respect to the femur. The CAS system can then perform 620 one or more kinematic simulations for the joint based upon the determined laxity information and collected pre-operative data. The kinematic simulations can be used to test a number of different implant configurations. For example, each simulation can include a different implant size or shape. The results of each of the kinematic simulations can be analyzed, and the CAS system can select 625 an optimized joint configuration. For example, an optimized joint configuration can include implant components that, when implanted in the patient, will likely produce the closest match to the patient's original range of knee motion based upon, for example, the pre-operative data and the laxity information.

Based upon the optimized joint configuration, the CAS system can generate 630 an updated surgical plan that accounts for any changes to the surgical procedure resulting from the optimized joint configuration and provide navigation data to the navigation system to guide preparation of the tibia and the femur to receive the implant components included in the optimized joint configuration.

In certain implementations, the CAS system can determine whether the position of the initial resection requires any changes to the surgical procedure as well. For example, if the depth or angle of the initial tibia resection is not accurate or might cause an issue with the originally selected implant components, the CAS system can determine what adjustments to the surgical procedure may be implemented to correct the potential issue. For example, the CAS system may alter the surgical procedure to change the position of the femoral implant component to accommodate any inaccuracies in the initial tibia resection. Additionally or alternatively, the CAS system may alter the surgical plan to use a different tibial implant component to accommodate any inaccuracies in the initial tibia resection. For example, if the initial tibia resection was deeper than the original surgical procedure required, a different size tibial implant component can be used to account for the added depth.

In other implementations, the CAS system may use the kinematic simulation to determine potential joint ranges of motion that rely on the initial tibia resection in comparison to ranges of possible motion if the surgeon was willing to perform a second tibia resection. The CAS system could provide metrics to the surgeon, allowing the surgeon to choose whether the advantage of the second resection's potential results outweigh the burden of making a second resection (resulting from, for example, increase surgical time).

In certain implementations, the CAS system can also provide instructions in the updated surgical procedure to recut or adjust the initial tibia resection. For example, the updated surgical procedure can include instructions for the surgeon to use a handheld navigated cutting tool such as a rotating bur to remove additional bone from the tibia to adjust the depth and/or angle of the initial tibia resection. The CAS system can navigate and control the cutting tool to accurately remove a particular amount of bone, thereby correcting and/or refining the initial tibia resection.

It should be noted that the process as shown in FIG. 6 is provided by way of example only. Additional steps can be performed depending upon the implementation of the procedure. For example, when attaching the tibia cut guide (e.g., as shown in FIG. 5), the position and angle of the cut guide can be accurately determined using a tracked measuring device such as a plate probe. The plate probe can be inserted into the guide slot on the cut guide, and the angle and depth of the cut guide can be accurately determined. In certain implementations, the cut guide may include means for adjusting the angle of the cut. For example, the cut guide may pivot about an rotational axis such that the angle of the cut is adjusted in specific increments such as one degree movements. By tracking the plate probe, the CAS system can provide an indication to the surgeon when the cut guide is properly angled for the initial cut. A similar process can be used for determining and adjusting the depth of the initial cut.

Figure 7:
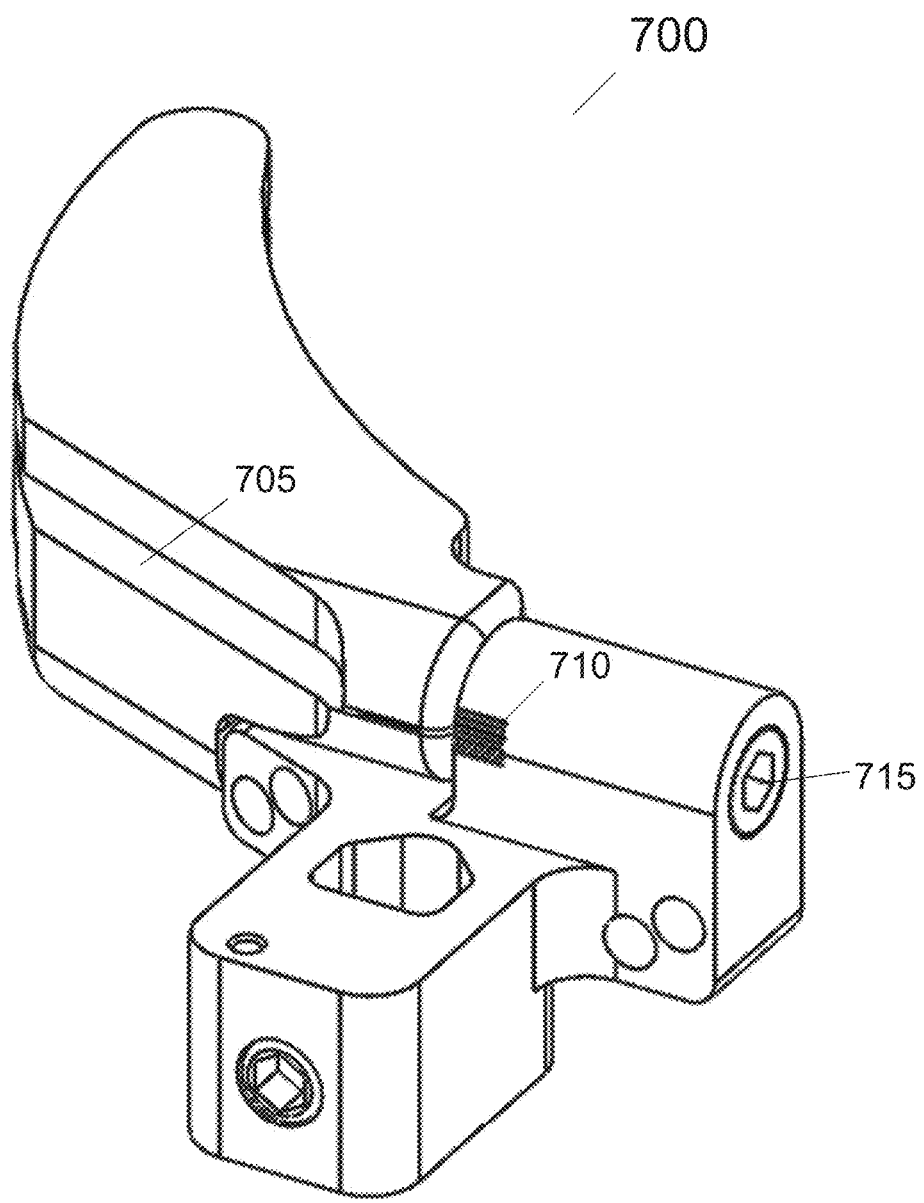
FIG. 7 illustrates a sample cutting guide having an adjustable slope in accordance with certain embodiments.

For example, as shown in FIG. 7, a cutting block 700 can be configured to include one or more features to alter or change the slope of the guide slot, thereby changing the angle of the resection. As shown in FIG. 7, the cutting block 700 includes a guide slot 705 that can be rotated about a fixed point to adjust the slope of the guide slot. The cutting guide 700 can also include markings 710 that are positioned to provide an indication of what angle the guide slot 705 is currently at. For example, as noted above, the markings 710 can indicate one degree movements of the guide slot 705. In certain implementations, the cutting guide 700 can include a locking feature 715 configured to lock the cutting guide at a particular angle. For example, the locking feature 715 can include a screw, a bolt, a pin, or another similar locking feature.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for tracking resection planes during a surgical procedure, the system comprising:
    an extramedullary alignment system comprising a guide rod;
    a cutting block configured to be mounted on an anterior surface of a bone during the surgical procedure, wherein the cutting block comprises at least one cut slot configured to position a resection tool during the surgical procedure and a receiving hole arranged and configured to receive the guide rod;
    a pivoting member connecting a first portion of the cutting block comprising the at least one cut slot and a second portion of the cutting block comprising the receiving hole, wherein the pivoting member extends along a coronal plane, and wherein the pivoting member is configured to facilitate rotation of a cut plane defined by the at least one cut slot along a sagittal plane;
    one or more markings indicating an angle of the rotation of the cut plane defined by the at least one cut slot along the sagittal plane; and
    a position tracker configured to directly couple to the cutting block after the cutting block is mounted on the anterior surface to allow positional tracking of the cutting block by a tracking device during the surgical procedure,
    wherein the at least one cut slot is further configured to be movable after the cutting block is mounted on the anterior surface to adjust a slope of the at least one cut slot,
    wherein the guide rod is configured to pass through the receiving hole such that the cutting block is translatable along the guide rod, and
    wherein the guide rod is substantially aligned to an axis of the bone.

2. The system of claim 1, wherein the position tracker comprises:
    a frame;
    one or more mounting points on the frame configured to be received by the receiving hole in a fixed orientation to couple the position tracker to the cutting block; and
    one or more position markers on the frame, each position marker being trackable by the tracking device during the surgical procedure.

3. The system of claim 2, wherein the one or more position markers are reflective to light.

4. The system of claim 2, wherein the one or more mounting points comprise a clamp.

5. The system of claim 1, further comprising a locking feature configured to lock a slope of the cutting block with respect to the anterior surface of the bone.

6. The system of claim 1, wherein the extramedullary alignment system further comprises an ankle clamp coupled to the guide rod, wherein the guide rod is configured to directly couple to the cutting block before the cutting block is mounted on the anterior surface, wherein the guide rod is configured to be aligned with an axis of the bone to position the cutting block, and wherein the ankle clamp is configured to be clamped to the bone when the guide rod is coupled to the cutting block.

7. The system of claim 6, wherein the receiving hole is arranged and configured to selectively receive: (i) the guide rod to couple the extramedullary alignment system to the cutting block during the alignment with the axis of the bone, and (ii) the position tracker in a rigid, fixed orientation, thereby coupling the position tracker to the cutting block during positional tracking of the cutting block by the tracking device.

8. The system of claim 6, wherein the guide rod includes a proximal end and a distal end,
wherein the proximal end of the guide rod is configured to directly couple to the cutting block before the cutting block is mounted on the anterior surface, and
wherein the distal end of the guide rod is coupled to the ankle clamp.

9. The system of claim 8, wherein the guide rod is configured to be aligned with the axis of the bone, such that an axis of the guide rod extending between the proximal end and the distal end of the guide rod is substantially parallel to the axis of the bone, to position the cutting block,
wherein the axis of the bone extends between a proximal end and a distal end of the bone.

10. The system of claim 6, wherein the ankle clamp is configured to be clamped at a distal end of the bone when the guide rod is coupled to the cutting block and the cutting block is mounted on the anterior surface at a proximal end of the bone.

11. The system of claim 1, further comprising a tracked probe comprising a plate configured to be inserted in the at least one cut slot, wherein an orientation of the plate is configured to be tracked by the tracking device during the surgical procedure.

12. A system for tracking a resection plane during a surgical procedure, the system comprising:
an extramedullary alignment system comprising a guide rod;
a cutting block configured to be mounted on an anterior surface of a bone, the cutting block comprising a receiving hole arranged and configured to receive the guide rod and at least one cut slot configured to position a resection tool during the surgical procedure, wherein the at least one cut slot is rotatable after the cutting block is mounted on the anterior surface to adjust a slope of the at least one cut slot with respect to the anterior surface, wherein the guide rod is configured to pass through the receiving hole such that the cutting block is translatable along the guide rod;
a pivoting member connecting a first portion of the cutting block comprising the at least one cut slot and a second portion of the cutting block comprising the receiving hole, wherein the pivoting member extends along a coronal plane, and wherein the pivoting member is configured to facilitate rotation of a cut plane defined by the at least one cut slot along a sagittal plane;
one or more markings indicating an angle of the rotation of the cut plane defined by the at least one cut slot along the sagittal plane;
a position tracker comprising a frame and a plurality of position markers disposed on the frame, wherein the position tracker is configured to directly couple to the cutting block after the cutting block is mounted on the anterior surface of the bone, and wherein the receiving hole is arranged and configured to receive a portion of the frame to rigidly couple the position tracker to the cutting block in a fixed orientation to enable positional tracking of the cutting block by a tracking device during the surgical procedure; and
a processor configured to:
receive, from the tracking device, a position of the plurality of position markers of the position tracker after the cutting block is mounted on the anterior surface of the bone,
receive, from the tracking device, an orientation of a plate of a tracked probe when the plate is inserted in the at least one cut slot, and
determine, based on the received position of the plurality of position markers and the received orientation of the plate, the resection plane for the resection tool through the at least one cut slot with respect to the anterior surface;
wherein the guide rod is substantially aligned to an axis of the bone.

13. The system of claim 12, wherein the resection plane for the resection tool is further determined based on a known geometric relationship between the plurality of position markers and the cutting block.

14. The system of claim 12, further comprising a tracking device including one or more sensors, the tracking device configured to:
detect the position of the plurality of position markers after the cutting block is mounted on the anterior surface of the bone, and
detect the orientation of the plate when the plate is inserted in the at least one cut slot.

* * * * *